US00PP28474P2

(12) United States Plant Patent
Lannes

(10) Patent No.: US PP28,474 P2
(45) Date of Patent: Oct. 3, 2017

(54) ***HIBISCUS* PLANT NAMED 'LANPLATTE'**

(50) Latin Name: *Hibiscus rosa-sinensis*
Varietal Denomination: Lanplatte

(71) Applicant: Robert M. Lannes, Malause (FR)

(72) Inventor: Robert M. Lannes, Malause (FR)

(73) Assignee: D.H.M INNOVATION, Malause (FR)

( * ) Notice: Subject to any disclaimer, the term of this patent is extended or adjusted under 35 U.S.C. 154(b) by 0 days.

(21) Appl. No.: 15/330,112

(22) Filed: Aug. 9, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hibiscus* named 'Lanplatte' that is characterized by its flowers that are dark red in color and flower centers (eye) that are darker red in color, its floriferous bloom habit with flowers that stay open for 2 to 3 days, its uniform, early blooming and freely flowering habit, its compact and self-branching plant habit and its foliage that is resistant to pathogens common to *Hibiscus*, including *Pseudomonas* sp., *Phythium* sp., and *Phytophthora* sp.

2 Drawing Sheets

Botanical classification: *Hibiscus rosa-sinensis.*
Cultivar designation: 'Lanplatte'.

BACKGROUND OF THE INVENTION

The present invention relates to a new and distinct cultivar of *Hibiscus rosa-sinensis* named 'Lanplatte' and will be referred to hereafter by its cultivar name, 'Lanplatte'. 'Lanplatte' is a new cultivar of tropical *Hibiscus* grown for use as a landscape and container plant.

The new cultivar was developed through an ongoing breeding program conducted by the Inventor in Malause, France. The objectives of the breeding program are to develop new cultivars of *Hibiscus* that exhibit bright colored flowers, a floriferous blooming habit with a high bud count and a self-branching and compact plant habit.

'Lanplatte' arose from a controlled cross made by the Inventor in July of 2009 between 'Vatican Rouge' (not patented) as the female parent and an unnamed proprietary plant from the breeding program; reference no. si 6522-1 (not patented) as the male parent. 'Lanplatte' was selected as a single unique plant from the resulting seedlings in September of 2013.

Asexual propagation of the new cultivar was first accomplished by stem cuttings in Malause, France in June of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Lanplatte' as a new and distinct cultivar of *Hibiscus.*

1. 'Lanplatte' exhibits flowers that are dark red in color and flower centers (eye) that are darker red in color.

2. 'Lanplatte' exhibits a floriferous bloom habit with flowers that stay open for 2 to 3 days.
3. 'Lanplatte' exhibits a uniform, early blooming and freely flowering habit.
4. 'Lanplatte' exhibits a compact and self-branching plant habit.
5. 'Lanplatte' exhibits foliage that is resistant to pathogens common to *Hibiscus*, including *Pseudomonas* sp., *Phythium* sp., and *Phytophthora* sp.

The female parent of 'Lanplatte' differs from 'Lanplatte' in having flowers that are lighter red in color, lower flower bud count, and in lacking a compact plant habit. The male parent of 'Lanplatte' differs from 'Lanplatte' in having flowers that are smaller in size and in being less floriferous with flowers that do not remain open as long. 'Lanplatte' can be most closely compared to the *Hibiscus* cultivars 'Heart Fire' (not patented) and 'Snow Queen' (not patented). 'Heart Fire' is similar to 'Lanplatte' in having glossy, evergreen leaves that are tolerant to heat and sun and in having large flowers that are red in color. 'Heart Fire' differs from 'Lanplatte' in having a less compact and more upright plant habit, flowers that are solid red in color that lack darker red centers and in having less self-branching. 'Snow Queen' is similar to 'Lanplatte' in having a floriferous blooming habit and flowers that are red in color. 'Snow Queen' differs from 'Lanplatte' in having variegated foliage and smaller flowers that are lighter red in color.

BRIEF DESCRIPTION OF THE DRAWINGS

The accompanying colored photographs illustrate the overall appearance and distinct characteristics of the new *Hibiscus*. The photographs were taken of an 18 month-old plant of 'Lanplatte' as grown in a two-gallon container.

The photograph in FIG. 1 provides a side-view of 'Lanplatte' in bloom.

Figure 1:
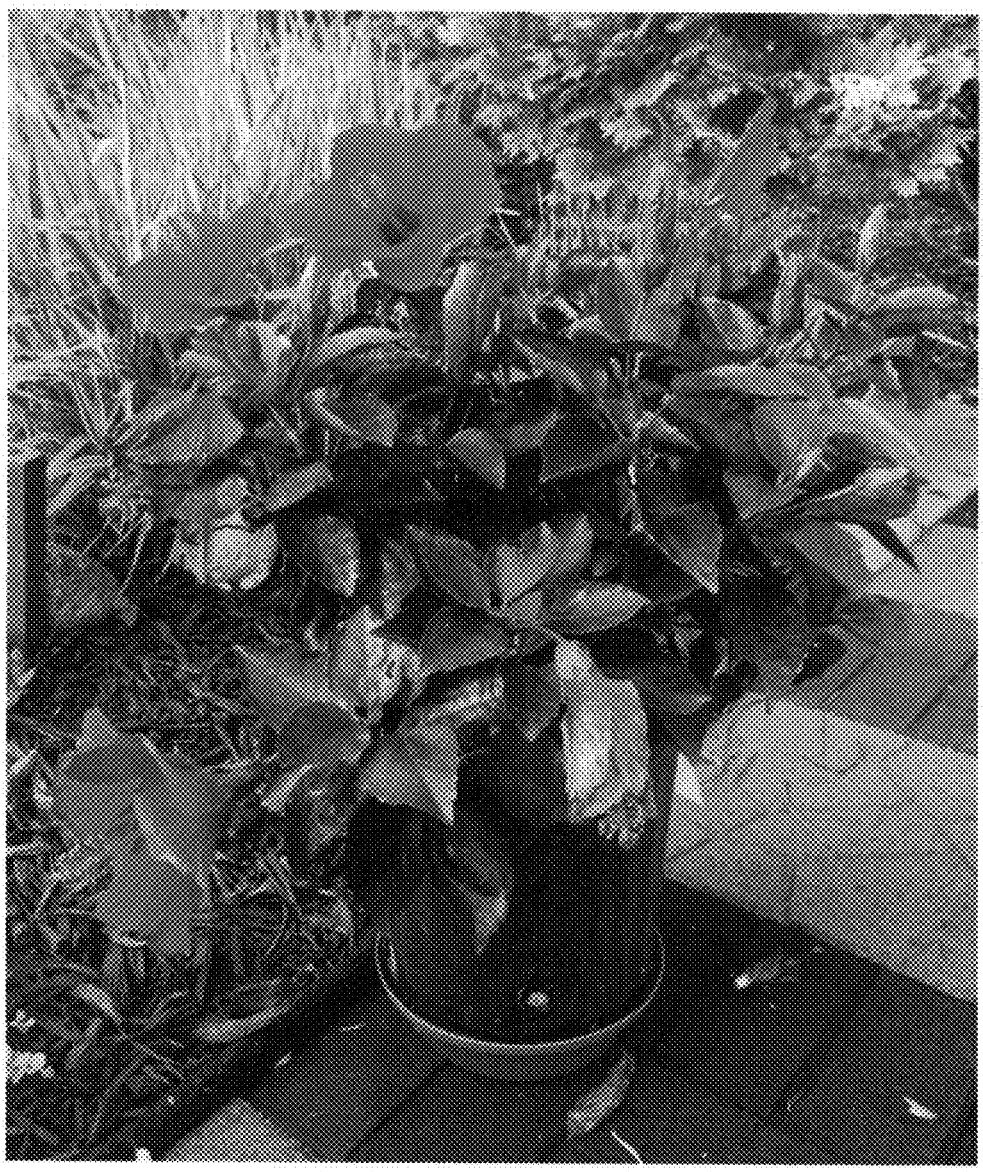
Figure 2:
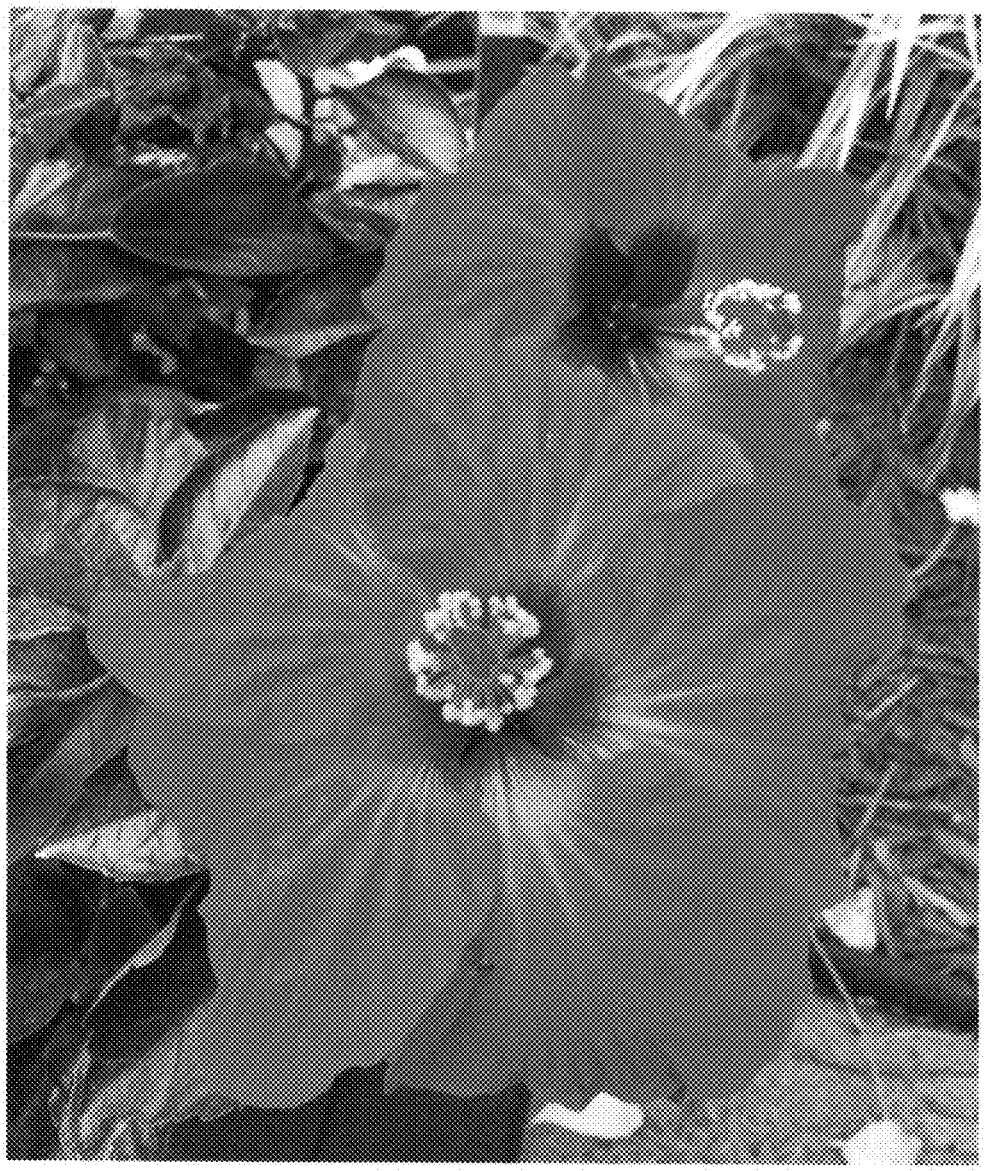

The photograph in FIG. 2 provides a close-up view of a flower of 'Lanplatte'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 18 month-old plants of the new cultivar as grown in two-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—Continuously producing in warm temperatures 55° F. to 90° F.

*Plant type.*—Tropical evergreen shrub.

*Plant habit.*—Compact and self-branching growth habit.

*Height and spread.*—An average of 34 cm in height and 38 cm in spread as grown in a one gallon container and reaches an average of 1.2 m in height and 1.5 cm in spread when mature.

*Hardiness.*—Tropical; at least in U.S.D.A. Zones 9 to 10.

*Diseases.*—Resistance to pathogens common to *hibiscus*, including *Pseudomonas* sp., *Phythium* sp., and *Phytophthora* sp.

*Root description.*—Fibrous roots, 156A in color.

*Propagation.*—Stem cuttings.

*Root development.*—Roots initiate in about 56 days and develop as a young plant in about 6 months.

*Growth rate.*—Moderately vigorous.

Stem description:

*Shape.*—Rounded.

*Stem color.*—New growth; NN137B, mature wood; 197B and 199C.

*Stem size.*—Main branches; data collection was taken from a mature plant had main stems pinched, average of 15 cm in length, up to 1.5 cm in width, lateral branches; average of 15 cm in length and 5 mm in width.

*Stem surface.*—New growth; Glabrous, mature wood; woody, finely striated, bark-like.

*Stem aspect.*—Held in multiple angles, growing upright to slightly outward.

*Stem strength.*—Strong.

*Branching.*—Heavy branching; an average of 5 main branches, an average of 15 lateral branches per main branch.

*Internode.*—Average of 1 cm.

*Stipules.*—1 to 2 per leaf node, varying between linear to lanceolate to obovate in shape, an average of 1 cm in length and 5 mm in width, acute apex, truncate base, outer surface; 136A in color, glossy and leathery texture, inner surface; 137A in color, shiny and matte texture.

Foliage description:

*Leaf shape.*—Varying between ovate and deltoid.

*Leaf division.*—Simple.

*Leaf base.*—Rounded and truncate.

*Leaf apex.*—Acute.

*Leaf venation.*—Pinnate, veins match leaf color.

*Leaf margins.*—Serrate and wavy.

*Leaf attachment.*—Petiolate.

*Leaf arrangement.*—Alternate.

*Leaf orientation.*—Upright, held in varying angles between 50° and 70° (90°=straight vertical).

*Leaf aspect.*—Varying between, flat and slightly curled upward with wavy margins.

*Leaf surface.*—Upper surface glabrous, glossy and leathery texture, lower surface very finely puberulent and matte texture.

*Leaf color.*—Young and mature leaves upper surface NN137A, lower surface 146A.

*Leaf size.*—An average of 7.5 cm in length, and 6 cm in width when mature.

*Leaf quantity.*—An average of 14 leaves per lateral stem, average of 22 cm in length.

*Petioles.*—An average of 2.5 cm in length and 2 mm in diameter, NN137B in color, surface is finely pubescent with a slight sheen overlay.

Flower description:

*Inflorescence type.*—Flowers are solitary from upper leaf axils.

*Lastingness of flowers.*—Average of 2 to 3 days, self cleaning.

*Flower size.*—An average of 6.5 cm in depth (including calyx) and 9 cm in diameter.

*Flower fragrance.*—None.

*Flower shape.*—Rotate.

*Flower number.*—An average of 3 flowers and buds present per stem at one time, continuously produces throughout the summer.

*Flower aspect.*—Outward when fully open.

*Flower bud.*—Elliptic in shape, surface of bud (petal section) is densely covered with pubescence 167A in color, surface color under pubescence is 183A, an average of 4.5 cm in length and 2 cm in width (including calyx).

*Petals.*—5, base 10% slightly fused, overlapping, oblanceolate in shape, an average of 6.5 cm in length and 5 cm in width, slightly serrate and wavy margins, rounded apex, base is cuneate, lower surface is shiny and waxy near the base (throat), upper surface is satiny and waxy near the base (throat), color of upper surface is N45A, blending to 53A at the base (throat), color lower surface is 45D, base is 157A.

*Calyx.*—Campanulate in shape, average of 3 cm in length and 2.5 cm in diameter.

*Epicalyx.*—Comprised of 7 bracts held upright surrounding sepals, lanceolate in shape, apiculate apex, truncate base, average of 1.5 cm in length and 4 mm in width, color of both surfaces is 144A, outer surface is dull and inner surface is glossy.

*Sepals.*—5, base 60% fused, an average of 1 cm in length and 1 cm in width, color of both surfaces is 144A, outer surface is dull and inner surface is glossy, acute apex, truncate base.

*Peduncles.*—An average of 6.5 cm in length and 3 mm in diameter, strong strength, average angle upright to outward, 144A, glabrous and glossy surface.

*Pedicels.*—Not present, flowers are solitary from terminal leaf axils.

*Receptacle.*—1 cm in diameter, 144B in color, glabrous and glossy surface.

Reproductive organs:

*Gynoecium.*—1 pistil, stigmas; 5, round in shape, 2 mm in diameter, fur-like surface and 53A in color, style arms; 3 mm in length, 42A in color, surface is pubescent and slightly glossy, style; average of 5.5 cm in length, very glossy surface, N45A, blending to 53A at the base, ovary; oblong in shape with pointed apex, 8 mm in length and 7 mm in width, 10B in color.

*Androecium.*—Stamens; average of 50, stamens are clustered and implanted into upper portion of style, anthers; dorsifixed and orbicular in shape, 2 mm in diameter, and 21A in color; filament; 4 mm in length and N34A in color, pollen; abundant in quantity and 21A in color.

*Fruit/seeds.*—Seed and fruit production has not been observed to date on plants of the new *Hibiscus.*

It is claimed:

1. A new and distinct cultivar of *Hibiscus* plant named 'Lanplatte' as herein illustrated and described.

* * * * *